(12) United States Patent
Schwind et al.

(10) Patent No.: US 8,841,082 B2
(45) Date of Patent: Sep. 23, 2014

(54) METHOD AND DEVICE FOR THE DETERMINATION OF MINOR CELL POPULATION IN HETEROGENEOUS CELL POPULATIONS

(75) Inventors: Peter Schwind, Fribourg (CH); Iwan Aebischer, Fribourg (CH)

(73) Assignee: Medion Diagnostics AG, Dudingen (CH)

(*) Notice: Subject to any disclaimer, the term of this patent is extended or adjusted under 35 U.S.C. 154(b) by 616 days.

(21) Appl. No.: 12/448,574

(22) PCT Filed: Dec. 14, 2007

(86) PCT No.: PCT/EP2007/011016
§ 371 (c)(1),
(2), (4) Date: Dec. 30, 2009

(87) PCT Pub. No.: WO2008/080544
PCT Pub. Date: Jul. 10, 2008

(65) Prior Publication Data
US 2010/0136585 A1 Jun. 3, 2010

(30) Foreign Application Priority Data
Dec. 29, 2006 (DE) .......................... 10 2006 062 619

(51) Int. Cl.
*G01N 33/00* (2006.01)
*G01N 33/558* (2006.01)

(52) U.S. Cl.
CPC .................................... *G01N 33/558* (2013.01)
USPC .......... 435/7.25; 436/514; 436/528; 436/535; 435/283.1; 435/7.1; 435/287.1; 435/287.2; 435/287.7

(58) Field of Classification Search
USPC .................. 436/514, 528, 535; 435/7.1, 7.25, 435/283.1, 287.1, 287.2, 287.7
See application file for complete search history.

(56) References Cited

U.S. PATENT DOCUMENTS 3,975,156 A * 8/1976 Kraft et al. ...................... 436/63
4,340,565 A * 7/1982 Kitajima et al. .............. 422/423
(Continued)

FOREIGN PATENT DOCUMENTS

DE         103 30 981      7/2003
WO    WO 98/39657          9/1998
(Continued)

OTHER PUBLICATIONS

Campbell et al., Cell Interaction Microarray for Blood Phenotyping, Mar. 2006, Analytical Chemistry, vol. 78, pp. 1930-1938.*
(Continued)

*Primary Examiner* — Melanie Y Brown
(74) *Attorney, Agent, or Firm* — McCarter & English, LLP; Steven G. Davis; Wei Song (57) ABSTRACT

The invention relates to a method for determining one or more cellularly bound analytes in a liquid sample, said method being carried out using a device comprising: at least one feeding zone (5) for applying the liquid sample; a porous membrane (2) that is suitable for letting cellular components penetrate therethrough and includes at least one indicator zone on the membrane, said indicator zone being able to interact with the cellularly bound analyte and containing at least one binding element against the cellularly bound analyte; and at least one absorption area (3) on the membrane, which absorbs the liquid after the liquid has passed the indicator zones. The at least one indicator zone lies between the feeding zone (5) and the absorption area (3). The method is carried out for concentrating and quantifying the minor cell population in heterogeneous cell populations, for example in cases of fetomaternal hemorrhage or in chimera, detecting an analyte provided at a low concentration on cells, determining the hematocrit value, and/or determining, in parallel, cellularly bound analytes in mixed-field reactions.

21 Claims, 6 Drawing Sheets

(56) References Cited

U.S. PATENT DOCUMENTS

| | | | |
|---|---|---|---|
| 4,943,522 A * | 7/1990 | Eisinger et al. | 435/7.25 |
| 5,432,054 A * | 7/1995 | Saunders et al. | 435/2 |
| 5,447,842 A * | 9/1995 | Simons | 435/6.11 |
| 6,203,757 B1 | 3/2001 | Lu et al. | |
| 6,303,390 B1 * | 10/2001 | Den Boer et al. | 436/520 |
| 7,858,757 B2 * | 12/2010 | Hollmann et al. | 530/388.22 |
| 2002/0173047 A1 * | 11/2002 | Hudak et al. | 436/178 |
| 2003/0143636 A1 * | 7/2003 | Simonson et al. | 435/7.9 |
| 2005/0124009 A1 * | 6/2005 | van Weeghel et al. | 435/7.21 |
| 2005/0170527 A1 * | 8/2005 | Boehringer et al. | 436/514 |
| 2007/0042499 A1 | 2/2007 | Schwind et al. | |
| 2007/0059782 A1 * | 3/2007 | Graham et al. | 435/7.21 |
| 2007/0248983 A1 | 10/2007 | Schwind et al. | |

FOREIGN PATENT DOCUMENTS

| | | |
|---|---|---|
| WO | WO 02/056019 | 7/2002 |
| WO | WO 2005/005966 | 1/2005 |
| WO | WO 2005/005991 | 1/2005 |
| WO | WO-2005005986 A1 | 1/2005 |

OTHER PUBLICATIONS

Ponsel, Dirk, "Mapping of Amino Acid Residues on the Hepatitis B Virus Capsid Involved in its Envelopment", English translation of the abstract, front page and page 10 of the Ph.D. Thesis of Dirk Ponsel, the Georg-August-University of Goettingen, Goettingen 2003.

Ponsel, Dirk, "Kartierung von umhüllungsrelevanten Aminosäureresten auf dem Hepatitis B Virus Kapsid", Dissertation, University of Göttingen, 2003, front page and p. 10.

* cited by examiner

METHOD AND DEVICE FOR THE DETERMINATION OF MINOR CELL POPULATION IN HETEROGENEOUS CELL POPULATIONS

This application is the U.S. National Stage of International Application No. PCT/EP2007/011016, filed Dec. 14, 2007, which designates the U.S., published in German, and claims priority under 35 U.S.C. §§119 or 365(c) to German Application No. 10 2006 062 619.2, filed Dec. 29, 2006. The entire teachings of the above applications are incorporated herein by reference.

FIELD OF THE INVENTION

The present invention relates to methods for the determination of minor cell populations in heterogeneous cell populations. Said methods are suitable for concentrating and quantifying the minor cell population in heterogeneous cell populations, for example in cases of fetomaternal hemorrhage; for determining in parallel cellularly bound analytes and, therefore, for determining both cell populations in mixed-field reactions after transfusion, in cases of fetomaternal hemorrhage or in chimeras; for detecting an analyte which is present at a low concentration on cells; and/or for determining the hematocrit value. The invention furthermore provides a device suitable for said method.

PRIOR ART

FMH

During a pregnancy, blood regularly passes from the fetal circulation into the maternal circulation (fetomaternal hemorrhage, FMH). According to the literature, this amounts to from 0.1 ml to about 30 ml; in approx. 96-98% of pregnancies, FMH is <2 ml, but in 0.3% of pregnancies, quantities of more than 30 ml are transferred. With the amount of maternal blood being estimated at 5000 ml, this means that 0.002% to 0.6% of a second type of erythrocytes with an antigen profile that deviates from that of the mother have entered the maternal circulation, and this becomes clinically relevant if it results in an immunization. The most prominent example is a D mother who is pregnant with a D+ fetus. If the mother produces anti-D antibodies, this may have fatal consequences in another pregnancy with a D+ fetus (hemolytic disease of the newborn, HDN). For this reason, the "anti-D prophylaxis" is administered to the mother in these situations. There is nonetheless great interest in being able to estimate the amount of FMH since, for example with an FMH of >30 ml, the standard anti-D therapy no longer gives sufficient protection. Thus, standard immunization in the USA comprises 250 to 300 µg of anti-D (IgG), which achieves sufficient prevention for a pregnant woman, in whose circulation 15 ml of fetal erythrocytes, i.e. 25 to 30 ml of fetal blood, have entered. The standard dose administered in Europe is often lower, namely from 100 to 150 µg of anti-D (IgG), giving protection with an FMH of 8-10 ml. Each institution that administers anti-D prophylaxis must employ a method which detects a larger-than-normal FMH (Issitt P D and Anstee D J. In: Applied Blood Group Serology [4th edition], Montgomery Scientific Publications, chapter 41: Hemolytic disease of the newborn, p. 1045-1050).

Conventional blood group-serology assays, for example for detecting the D antigen, cannot even come close to detecting such small amounts of a second population as described above.

There are, therefore, a number of distinct assays which have been developed especially for detecting an FMH. Said assays detect fetal erythrocytes, the blood group D antigen or hemoglobin F.

FMH Detection Assays: FMH Detection Limit

Rosette Test: Approx. 10 ml

This assay is based on detecting erythrocyte aggregates and the microscopic evaluation thereof. Detection of the fetal D antigen.

(Jones A. R., Silver S. Blood 1958; 13: 763 Sebring E. S., Polesky H. F. Transfusion 1982; 22: 468 Sebring E. S. In: Hemolytic disease of the newborn. Arlington, Va.; Am Assoc Blood Banks 1984: 87.)

Kleihauer-Betke Test: Approx. 5 ml

This assay is based on the higher resistance of fetal erythrocytes to elution with acid and the microscopic evaluation thereof. Detection of fetal cells.

(Kleihauer E., Braun H., Betke K. Klein Wschr 1957; 35: 637.)

Flow Cytometry Approx. 1 ml

D antigen or hemoglobin F is labeled with corresponding antibodies and detected via a fluorescent second antibody. Detection of the fetal D antigen/hemoglobin.

Garratty G., Arndt P. Transfusion 1995; 35: 157.

David B. H. Clin Lab Med 2001; 21: 829.

Antibody Consumption Assay: Approx. 15 ml

This assay is the first assay for determining an FMH that is designed on the basis of a routine method of determining blood groups (gel technology). It is based on the consumption of anti-D reagent by fetal erythrocytes. The reaction supernatant is incubated with D-positive test cells and centrifuged in the gel test. Detection of the fetal D antigen.

Lapierre Y., Rigal D., Adam J., Josef D., Meyer F., Greber S., Drot C. Transfusion 1990; 30: 109.

David M., Stelzer A., Wittmann G., Dudenhausen J. W., Salama A. Z. Geburtshilfe Neonatol 1999; 203: 241.

These assays are used for detecting erythrocytic antigens, fetal erythrocytes or hemoglobin F which is characteristic of fetal erythrocytes. All of these methods share the fact that performing them requires numerous reagents as well as both time and effort. Furthermore, all methods are characterized in that performing them requires instruments, some of which are very expensive (microscope, centrifuge, flow cytometer). Said methods also share the fact that specially trained staff are needed for performing them. The Kleihauer-Betke assay has the additional disadvantage that evaluating the results is very subjective.

Weak D Feature Expressions (Dweak), in Particular DEL

Another challenge to the serology of donors and receivers are weak or partial expressions of the D antigen. Owing to monoclonal antibodies and confirmation in the indirect Coombs test, typing even of such weak blood groups appeared to be secure, until the DEL phenotype was described which has a particularly weak D expression ("normal" D: 10-30 000 antigens per erythrocyte (RBC); D weak: 400 to 1000; DEL: <30).

Serologically, DEL can be detected only indirectly using extremely complicated adsorption-elution tests comprising up to 10 washing steps. DEL is of relevance to transfusion medicine, since D receivers of stored blood of a DEL person can form anti-D antibodies. This problem is so serious that there is currently a discussion among experts, as to whether the D status of all (serological) D donors should be verified by molecular methods.

Wagner T., Körmöczi G. F., Buchta C., Vadon M., Lanzer G., Mayr W. R., Legler T. J. Transfusion 2005; 45:520.

Mixed-Field Reactions, Homologous Transfusion, Blood Doping

Transfusions should always be administered with the same or compatible ABO and compatible D. In certain cases, for example with pretransfused patients, it is clinically indicated to transfuse the same blood group also for other antigens. However, it is never possible to transfuse the same blood group in all blood groups (exception: autologous transfusion). This regularly results in the post-transfusion situation that a person is diagnostically positive and negative for certain blood group features. In diagnostics, "mixed-field reactions" are found, such as can also be readily detected by sensitive methods—in particular those capable of spatially separating individual erythrocytes and hemagglutinates during detection. If, for example, 300 ml (67%) of an erythrocyte concentrate are administered to a K-negative person (blood group kk), whose circulation has 5000 ml of blood (hematocrit of 45%), and the concentrate is K+ (blood group Kk or KK), then nominally around 8% of the erythrocytes of said person are K+ and 92% of the erythrocytes are K−.

Such a situation can still be detected, for example, by the now widely used gel systems from DiaMed and Bio-Rad. This technology involves centrifuging a diluted suspension of the erythrocytes of the person to be examined through a gel-chromatographic column which is closed at the bottom and which may contain antibody reagents of different specificities. Free, non-agglutinated cells are capable of passing through the gel and form a sediment at the bottom of the reaction vessel, while hemagglutinates are retained on or in the gel (Lapierre Y., Rigal D., Adam J., Josef D., Meyer F., Greber S., Drot C. Transfusion 1990; 30: 109). If the erythrocytes of the example are centrifuged through such an anti-K-containing column, most of the cells will sediment at the bottom because they are K−, and a small portion will be retained on or in the gel (K+), corresponding to the detection of the mixed field illustrated above. If such erythrocytes as above are applied to MDmulticard (Medion Diagnostics), a weak band at anti-K is likewise detectable. However, in contrast to gel technology, the method disclosed in WO2005005991 cannot make visible the negatively reacting cell population at the same time. All other methods of the prior art do not have any properties comparable to the gel systems and MDmulticard for detecting mixed-field reactions.

Homologous Transfusion and Blood Doping:
Nelson M., Popp, H., Sharpe K., Ashenden M. Haematologica 2003; 88: 1284.
Mixed-Field Reactions after Transfusion:
Issitt P. D. and Anstee D. J. In: Applied Blood Group Serology (4th edition), Montgomery Scientific Publications. Chapter 3: Hemolytic disease of the newborn. p. 1045-1050.
Hematocrit The hematocrit or total volume of erythrocytes is the ratio of the volume of erythrocytes to the total volume of whole blood, expressed as a percentage. The volume ratio of erythrocytes to whole blood is influenced by the volume and the number of erythrocytes.

The hematocrit can be determined typically by centrifugation of blood-filled capillaries (Strumia M. M., Sample A. B., Hart E. D., 1954; Am J Clin Path; 24: 1016) in that, after centrifugation, the ratio of the proportion of sedimented cellular components to the total volume is formed. The hematocrit can also be determined with the aid of electrical impedance methods. Here, the current flowing in an electrolyte solution between anode and cathode is influenced by particles of different conductivity which are introduced into said current. The changes in current are recorded as pulses. A particular particle size and thus, in hematology, a particular cell type, for example erythrocytes, can be inferred from a particular pulse amplitude. The cell number and the hematocrit can be derived from adding up pulses per volume measured (Sysmex KX-21N Operator's Manual, 1999).

It is therefore an object of the present invention to provide simple, cost-effective, automatable methods delivering quick results for determining the minor cell population in heterogeneous populations, as in cases of fetomaternal hemorrhage or in chimeras. The invention is also intended to provide simple, rapid and sensitive methods for detecting an analyte which is present at a low concentration on cells, for determining the hematocrit value and/or for determining in parallel cellularly bound analytes in mixed-field reactions. Said methods should preferably have increased sensitivity over known methods.

BRIEF DESCRIPTION OF THE INVENTION

The objects stated above are solved by providing a method for determining one or more cellularly bound analytes in a liquid sample, said method being carried out using a device comprising:
at least one feeding zone (5) for applying the liquid sample,
a porous membrane (2) that is suitable for being penetrated by cellular components and that includes at least one indicator zone on the membrane, which indicator zone can interact with the cellularly bound analyte and contains at least one binding element against the cellularly bound analyte, and
at least one absorption area (3) on the membrane, which absorbs the liquid after the latter has passed the indicator zones,
wherein the at least one indicator zone is located between the feeding zone (5) and the absorption area (3), and wherein the method is carried out for concentrating and for quantifying the minor cell population in heterogeneous cell populations, for example in cases of fetomaternal hemorrhage or in chimeras, for detecting an analyte which is present at a low concentration on cells, for determining the hematocrit value and/or for determining in parallel cellularly bound analytes in mixed-field reactions.

In a preferred embodiment, the method comprises the steps of:
a) applying a sample containing cells to the feeding zone;
b) applying a diluent;
c) performing the assay; and
d) evaluating the assay by determining whether cells are bound to the indicator zone.

The method according to this preferred embodiment is preferably carried out for concentrating and for quantifying the minor cell population in heterogeneous cell populations, for example in cases of fetomaternal hemorrhage, or for detecting an analyte which is present at a low concentration on cells.

Said embodiment is also referred to as "incubation method" hereinbelow.

DE 10330982 A1 and WO2005/005986 have disclosed a lateral flow device. The latter is used therein for the simultaneous determination of erythrocytic antigens and serum components such as antibodies. The lateral flow device disclosed in this printed publication is suitable for the methods stated according to the invention. The disclosures of DE 10330982 A1 and WO2005/005986 are hereby incorporated in their entirety.

Said lateral flow device is utilized according to the invention as flow cytometer in order to be able to concentrate to a maximum a second cell population present in a small amount in a heterogeneous cell mixture. Said concentration is preferably carried out quantitatively by utilizing a maximum total amount of blood, and qualitatively by means of an incubation effect caused by an increase in volume. The reading field in the lateral flow device is similar to the flow cell in a flow cytometer. The background is kept low by washing out the cell type present at a higher concentration and immobilizing the lower concentration cell type in the reading window.

As a result, a sufficiently large number even of a low-proportion population passes the antibody band, so that also this population can be rendered visible. This is made possible by washing out a large portion of the distinctly over-proportional population.

The present method applied to determining FMH is highly sensitive and enables from approx. 0.1% to 0.2% of fetal D+ cells to be detected in the maternal blood.

According to another preferred embodiment, the device used in the method contains at least two indicator zones which are arranged one behind the other in the direction of flow in such a way that the sample liquid passes through more than one indicator zone in each flow track, wherein the indicator zones contain binding elements against cellularly bound analytes, and the method comprises:
a) applying a blood sample containing erythrocytes to the feeding zone;
b) applying a diluent to the feeding zone;
c) performing the assay;
d) evaluating the assay by determining whether erythrocytes are bound to the indicator zone(s),
wherein the method is carried out for determining in parallel cellularly bound analytes in cases of fetomaternal hemorrhage (FMH), for determination in mixed-field reactions, for detecting a homologous transfusion or for determining the hematocrit value.

This embodiment is also referred to as "two-indicator zone method" hereinbelow.

According to a further aspect of the present invention, a device is provided for directly determining cellularly bound analytes in a liquid sample, which device comprises:
  a feeding zone (5) for applying the liquid sample,
  a porous membrane that is suitable for being penetrated by cellular components and includes at least two indicator zones on the membrane, which indicator zones can interact with the cellularly bound analyte(s), and which contain binding elements against cellularly bound analytes, and
  at least one absorption area (3) which absorbs the liquid after the latter has passed the indicator zones,
wherein the indicator zones are located between the feeding zone (5) and the absorption area (3), wherein the at least two indicator zones are arranged one behind the other in the direction of flow in such a way that the sample liquid passes through more than one indicator zone in each flow track.

The lateral flow device provided according to the invention differs from that of WO2005/005991 in that it has, according to the invention, in the preferred embodiment illustrated herein, two indicator zones located one behind the other, in order to enable both cell populations in a mixed field to be made visible at the same time. The sensitivity for detecting a mixed field is higher than that of the only previous routine method by which mixed fields can be detected, namely gel technology (DiaMed). The sensitivity of the method according to the invention enables a minor cell population to be detected, if its proportion is approx. 1-2% of the total population.

The method and the device enable mixed-field agglutinations to be detected with high sensitivity. This usability is also surprising because a person skilled in the art would have assumed that the first indicator zone, after binding of the analyte-bound cells, would act as a diffusion barrier to binding to the second indicator zone.

The lateral flow device can be utilized for hematocrit determination as a flow cytometer which has at least two indicator positions located one behind the other, in order to be able to detect the erythrocyte concentration of a blood sample. The higher said concentration, the more points of a line give a positive signal. The method may be extended to a 2D array by placing a plurality of flow tracks with, for example, in each case 5 anti-erythrocyte points side by side, with the individual flow tracks having increasing or decreasing anti-erythrocyte concentrations.

The use of the lateral flow device also enables blood group and hematocrit to be determined in parallel.

FIGURE LEGENDS

FIG. 4A here depicts the result of the examination of a blood sample with 100% A cc D. ee and 0% B CC D. EE. FIG. 4B depicts the result of the examination of a blood sample with 98% A cc D. ee and 2% B CC D. EE.

DETAILED DESCRIPTION OF THE INVENTION

Definitions

In the context of the present invention, the following terms should be understood as illustrated below:

The term "minor cell population in heterogeneous cell populations" means that a cell population is present in a low amount or concentration in comparison with one or more other cell populations which are also present in the heterogeneous cell populations. The concentration of the minor cell population, based on the total heterogeneous cell population, here is less than 50%, preferably less than 10%, particularly preferably less than 1%, in particular less than 0.1%.

The term "homologous transfusion" means transfusions which are compatible in the essential features; the more features are checked after such a transfusion, the more likely it is to be able to detect via mixed fields that transfusion has occurred. This probability can be maximized by the selection of the features to be determined. Such determinations are used for convictions of illegal blood doping by homologous transfusion.

The term "autologous transfusion" means self-donation of blood, with donor and receiver here being, per definitionem, identical in all features.

The term "mixed field": Since transfusions, apart from autologous transfusion, cannot have the same blood groups with respect to all antigens, mixed fields are produced in serology with respect to differing antigens between stored blood and receiver.

The term "DEL": this is a particularly weakly expressed D feature with <30 antigens/cell. This can no longer be detected by commercial serological methods.

The term "hematocrit" means the proportion of erythrocytes [%] of the total blood volume. The following averages are observed: men: 44-52%; women: 37-47%.

The term "chimera" is used for an organism whose cells represent two or more zygotes.

Preparation of the Lateral Flow Device

In principle, any lateral flow devices specified in DE 10330982 A1 and WO2005/005986 are suitable.

The membrane of the device used according to the invention is a porous membrane. Preferred examples of membrane materials are nitrocellulose (for example UniSart by Sartorius, HiFlow by Millipore, Whatman, AE99 and FF85/100 by Whatman Schleicher & Schuell), polyethylene (Lateral Flo by Porex Corporation or nylon (Novylon by CUNO). The membrane preferably has a very large pore size because a high porosity of the membrane benefits penetration, in particular of cellular components of the sample to be determined, for example of erythrocytes, into the porous structure. Particularly advantageous is the use of absorbing membranes. However, the device of the invention is not limited to these properties. Preference is given to any membranes having a high capillary flow rate (capillary speed), which is the time needed by a dye solution to travel 40 mm on a given membrane. Particular preference is given to membranes whose capillary flow rate is <100.

In a preferred embodiment of the invention, a sealing element is arranged in the direction of flow on the porous membrane downstream of the feeding zone of the device according to the invention. Use is made of two- or three-dimensional sealing elements which are placed on the porous membrane and which are used for generating a sample application zone separated from the remaining surface of the porous membrane. According to the invention, the sealing element acts primarily as a liquid barrier and allows sample liquid and test reagents to be distributed into the porous membrane in a directed manner. Furthermore, according to the invention, the sealing element seals off the sample application zone to prevent an undesired transfer of liquid into the other areas of the lateral flow device.

In preferred embodiments, the sealing element is web- or trough and/or funnel-shaped. The sealing element is formed by cutting processes from the material used for manufacturing the sealing element. In the case of the funnel and trough shapes, the sealing element is provided with an inner opening whose preferred embodiment variations are round, square or rectangular shapes which, in the case of the funnel shape, taper toward the bottom side (membrane contact side) of the sealing element.

Preferred materials for the sealing element are materials which do not absorb water (hydrophobic materials). In a particular embodiment, the materials are coated on one side with an adhesive film, for example a pressure-sensitive or self-adhesive acrylate adhesive. The sealing element can thus be glued directly onto the surface of the porous membrane. Alternatively, the sealing element may be connected, for example bonded, to the lateral flow housing, wherein in this embodiment the lateral flow housing presses the sealing element onto the surface of the porous membrane, thereby attaining the functions of said sealing element.

Preferred materials for producing two-dimensional sealing elements are any form of adhesive tapes or adhesive films (for example Tesa 4124 by Beiersdorf AG, ARcare 7815 by Adhesives Research).

Preferred materials for producing three-dimensional sealing elements are flexible, closed-pore elastomeric materials or flexible silicone materials having different material thicknesses, preferably 3-5 mm (for example closed cell rubber EPDM140 by Pitzner, silicone rubber or non-cellular rubber, 40° hardness or less, by Castan).

In a further preferred embodiment, multiple sealing elements consisting of one piece with, for example, 20 individual cavities (trough shape) are arranged on a membrane.

Due to this design according to the invention, the device of the invention is capable of taking up liquid samples containing cells, such as whole blood for example, without said cells being filtered off in the process. The sealing element furthermore allows large sample volumes to be applied to the porous membrane (feeding zone), without the latter being flooded. The sealing element thus supports the utilization of the absorbing properties of the porous membrane. The sealing element further guarantees a directed sample flow. However, the device according to the invention is capable of working well with or without sealing element.

For the absorption area (absorption pad) of the device according to the invention, preference is given to mechanically stable materials which preferably have water absorption capacities of 20-30 g/100 cm$^2$ (e.g. Wicking Paper, Type 300, Whatman Schleicher and Schüll). Contact between the absorption pad and the lateral flow membrane of the device according to the invention is achieved by pressing down and overlapping with the porous membrane. The exact positioning of the absorption pad on the membrane is achieved by bonding the absorption pad to the support layer (backing sheet) supporting the lateral flow membrane.

In a further embodiment, the components of the device according to the invention are applied to a backing sheet or support layer for the purpose of mechanical reinforcement. However, the device according to the invention is capable of functioning with or without support layer. Preference is given to mechanically stable materials which do not absorb water and which preferably have material thicknesses of 100 μm or more and which are coated on one side or on both sides with an adhesive film, for example a pressure-sensitive or self-adhesive acrylate adhesive (e.g. 0.005" Polyester W/GL-187, G & L). The porous membrane and the absorption pad are fixed to the support layer. In the case of the double-sided adhesive support layer, the adhesive second side is used for fixing the stack on other surfaces, for example inside the lateral flow housing.

In a further embodiment, the device according to the invention, either with or without support layer, to which the components of the device according to the invention have been applied, is integrated in a housing, whereby the membrane components are pressed against each other and said housing supports the sealing element function. However, the device according to the invention may function equally well both with and without housing.

Incubation Method

According to a preferred embodiment, the method is carried out for determining fetomaternal hemorrhage (FMH), wherein the sample contains erythrocytes, wherein the indicator zone preferably contains an antibody or an antibody mixture.

The sample containing cells may be any sample. The cells are preferably cells present in the blood, such as erythrocytes, leukocytes or thrombocytes. Preference is given to the cells being erythrocytes. The sample containing erythrocytes may here be selected from a whole blood or blood cell concentrate. The blood cell concentrate here may be a resuspended erythrocyte sediment.

Preference is given to using more than 200 µl of whole blood, markedly exceeding the number of cells usually applied to lateral flow devices. Due to the high number of cells made available to the system, the total number of the minor cell population passing through the flow cytometer also increases, thus resulting in better detectability.

The diluent may in principle be any diluent known in the prior art. The diluent is preferably selected from physiological saline, Diluent 1, Diluent 2 (DiaMed), Diluent F (Medion Diagnostics). It is used for diluting the cells, preferably in the 100 µl to 200 µl range. In contrast to methods disclosed previously, the proportion of diluent of the total suspension is preferably lower than that of the whole blood or erythrocyte sediment used, so as to effect a relatively high cell concentration and a low flow of erythrocytes.

Performing the assay comprises incubating over a sufficient period of time, in order for the applied sample to migrate from the feeding zone through the indicator zone(s) to the absorption area.

The assay may be evaluated by the naked eye or in an automated way.

The indicator zones of the device according to the invention are located on the membrane and comprise binding elements which capture or bind the analytes to be determined in the sample. The binding reactions between analyte and binding element are detected in the indicator zones. Particularly preferred binding elements that are attached to the porous membrane are antibodies or antibody fragments or lectins. The indicator zones preferably comprise in each case a binding element against an analyte to be investigated. The indicator zones may be in the shape of spots, lines and/or wedges. Preference is given to the line-shaped design in the direction of flow. The minor cell population is preferably detected by a wedge-shaped design of the indicator zone, which enables superior recognizability.

According to a further preferred embodiment, the method is carried out for determining an analyte which is present at a low concentration on cells, preferably the blood group DEL, and the indicator zone preferably contains an antibody or an antibody mixture.

The method according to the invention may further comprise prior to step a), preparing an erythrocyte sediment by centrifuging the blood sample; incubating the sediment with a bromelain, papain or ficin solution and resuspending the enzyme-treated sediment (as described, for example, in AABB Technical Manual, 14th edition, 2003, 693 ff.). The incubation is carried out over a period of from 5 to 60 minutes. The enzymes to be used are commonly commercially available.

An advantage of enzymatic pretreatment is a stronger exposition of the D antigens to the erythrocytes and therefore a higher sensitivity of the determination.

In the method of the invention (variant incubation methods), preference is given to applying in step a) approximately from 100 µl to 500 µl of blood sample or resuspended erythrocyte sediment. This markedly exceeds the amount of particles and volume normally applied to lateral flow devices.

In the method of the invention, preference is given to applying in step b) approximately from 100 µl to 200 µl of diluent. The enlarged total volume of liquid results in a slower flow, leading to a quasi-incubation of the analyte with the indicator zone.

If the indicator zone contains an anti-D antibody, then the latter is preferably selected from RUM-1, LDM-3, ESD1M, TH-28, MS-201, MS-26 and LDM-1, as are commercially available from Millipore or Alba Bioscience. It is also possible, however, to use antibody mixtures or else affinity-purified polyclonal antisera.

Two-Indicator Zone Method and Device

The above explanations regarding the incubation method also apply to the two-indicator zone method, unless defined differently below.

In a preferred embodiment, the method is carried out for determining the hematocrit value, wherein the indicator zone preferably contains an antibody or an antibody mixture and the overall pattern in which the erythrocytes are bound to the indicator zones is determined in step d).

In a further preferred embodiment of the method, the device contains at least two indicator zones arranged in a single flow track, and wherein the indicator zones contain identical binding elements against the same cellularly bound analyte.

This embodiment of the invention contains more than one such series of indicator zones. The indicator zones may be in the shape of spots, lines and/or wedges. Preference is given to the line-shaped design in the direction of flow. Advantageously, the minor cell population is detected by a wedge-shaped design of the indicator zone, which enables superior recognizability. The two-indicator zone method enables the minor cell population to be depicted in addition to the major cell population, with a proximal location, with respect to the feeding zone, of the indicator zone which is directed against the minor cell population. Particular preference is given to an arrangement in which the in each case proximal indicator zone of the two indicator zones in a single flow track is applied as a line in the direction of flow and the in each case distal indicator zone is applied as a spot.

In a preferred embodiment, at least two flow tracks containing in each case at least two indicator zones filled with different binding elements are located on the membrane.

In a further preferred embodiment of the method, the device has at least two flow tracks containing at least two indicator zones, and the concentration of the binding element increases or decreases from proximal to distal, in relation to the feeding zone. This enables the amount of erythrocytes present in the sample to be assessed quantitatively in relation to the total volume and thereby the hematocrit to be determined approximately.

Preference is furthermore given to the device having at least two flow tracks containing at least two indicator zones, and the concentration of the antibody spots in a first flow track differs from the concentration in a second flow track.

According to a further preferred embodiment, the method of the invention is carried out for determining in parallel cellularly bound analytes in mixed-field reactions or for detecting a homologous transfusion, wherein the device here contains at least two indicator zones which are arranged one behind the other in the direction of flow in such a way that the sample liquid passes through more than one indicator zone in each flow track, wherein the indicator zones contain binding elements against different cellularly bound analytes.

Preference is given to the cellularly bound analyte being selected from a blood group antigen such as A, B, AB, D, C, c, E, e, Cw, K, k, Jka and/or Jkb. Particular preference is given to the blood group antigens being determined by way of the reaction pairs A, B; D+, D−; K, k; C, c and/or E, e.

The binding element directed against the analyte, as defined above for the incubation method, is preferably selected from an antibody, antibody fragment, lectin, lectin fragment or mixtures thereof.

According to a further aspect of the present invention, a device is provided for carrying out the above-described two-indicator zone method.

EXAMPLES

Example 1

Determination of Mixed-Field Reactions

Preparation of the test strips: with serial application of in each case 2 different antibodies:

The test strips consist of a central feeding zone, two indicator zone areas and two absorption areas. Membranes of the Millipore HiFlow Plus 075 type are cut into strips to a size of 19×75 mm (width/length; y/x) for a 10-pair design and glued onto a support layer (backing sheet, for example by G&L). A central feeding zone is used (bidirectional flow), and 0.3 µl lines and 0.1 µl spots, respectively, of solutions of various blood group-specific monoclonal antibodies are applied in the indicator zone area in parallel rows on both sides of the feeding zone, using a dispenser, for example AD3200 (Biodot), with serial application of in each case 2 different antibodies, one of which as a spot and the other as a line:

Anti-A-clone Birma-1 (Millipore, TL); anti-B-clone LB-2 (Millipore, TN); anti-D-clone LDM3 (Alba Bioscience, Z7180100); anti-C-clone MS-24 (Millipore, FFMU, KG); anti-c-clone MS-33 (Millipore, KN); anti-E-clones MS-80+MS-258 (Millipore, TA); clones anti-e MS-21+MS-63 (Millipore, FFMU, KL+KQ); anti-K-clone MS-56, (Millipore, KO); anti-k (AlbaClone, Alba Bioscience). Anti-RBC (Rabbit IgG Fraction of anti Human RBC, Rockland, 209-4139).

The antibodies applied as spots are positioned in position x=22 mm (to the left of the feeding zone) or in position x=53 mm (to the right of the feeding zone), starting at 3.5 mm from the top side of the membrane, in each case spaced at 3 mm along the y axis. The antibodies applied as lines are positioned in position x=25-28 mm (to the left of the feeding zone) or in position x=37-50 mm (to the right of the feeding zone), starting at 3.5 mm from the top side of the membrane, in each case spaced at 3 mm along the y axis. The antibodies are diluted in 15 mM potassium phosphate buffer pH 7.5, 10% (v/v) methanol, as follows: anti-A antibody 1:3, anti-B antibody 1:2, anti-AB antibody 1:4, anti-D antibody 1:4, anti-RBC antibody 1:3. All other antibody solutions are not prediluted but are mixed with methanol to 10% (v/v).

After dispensing the antibodies, the membranes are dried at 40° C. for 20 min and then stored at constant humidity until the test is performed. A 19×20 mm absorption pad (Whatman Schleicher & Schüll, 300) overlapping the membrane by 3 mm is glued on at both ends distal to the feeding zone. The feeding zone is separated from the remaining membrane over the entire width of said membrane by gluing on a trough-shaped sealing element (closed cell rubber EPDM140 by Pitzner) in position y=32.5-37.5 mm.

| Proximal (line) | Distal (spot) |
|---|---|
| To the left of the feeding zone: | |
| Anti-A → | Anti-B |
| Anti-B → | Anti-A |

| Proximal (line) | Distal (spot) |
|---|---|
| Anti-D → | Anti-RBC |
| Anti-RBC → | Anti-D |
| Anti-K → | Anti-k |
| To the right of the feeding zone: | |
| Anti-C → | Anti-c |
| Anti-c → | Anti-C |
| Anti-E → | Anti-e |
| Anti-e → | Anti-E |
| Anti-k → | Anti-K |

Figure 1:
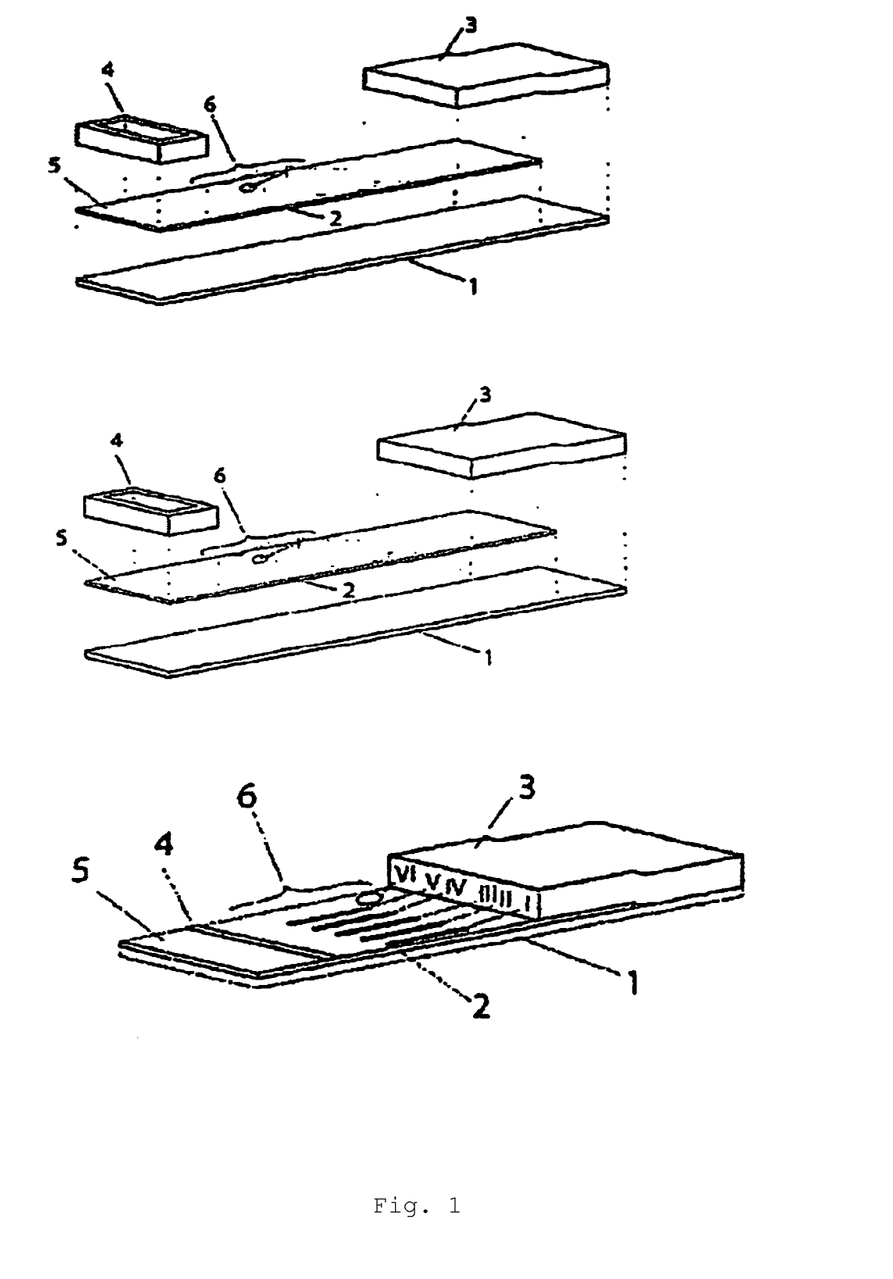
FIG. 1 depicts a diagrammatic representation of a device suitable for carrying out the above-described incubation method. The reference signs have the following meaning: (1) support layer; (2) porous membrane; (3) absorption area; (4) sealing element; (5) feeding zone; and (6) indicator zone area.
Figure 2:
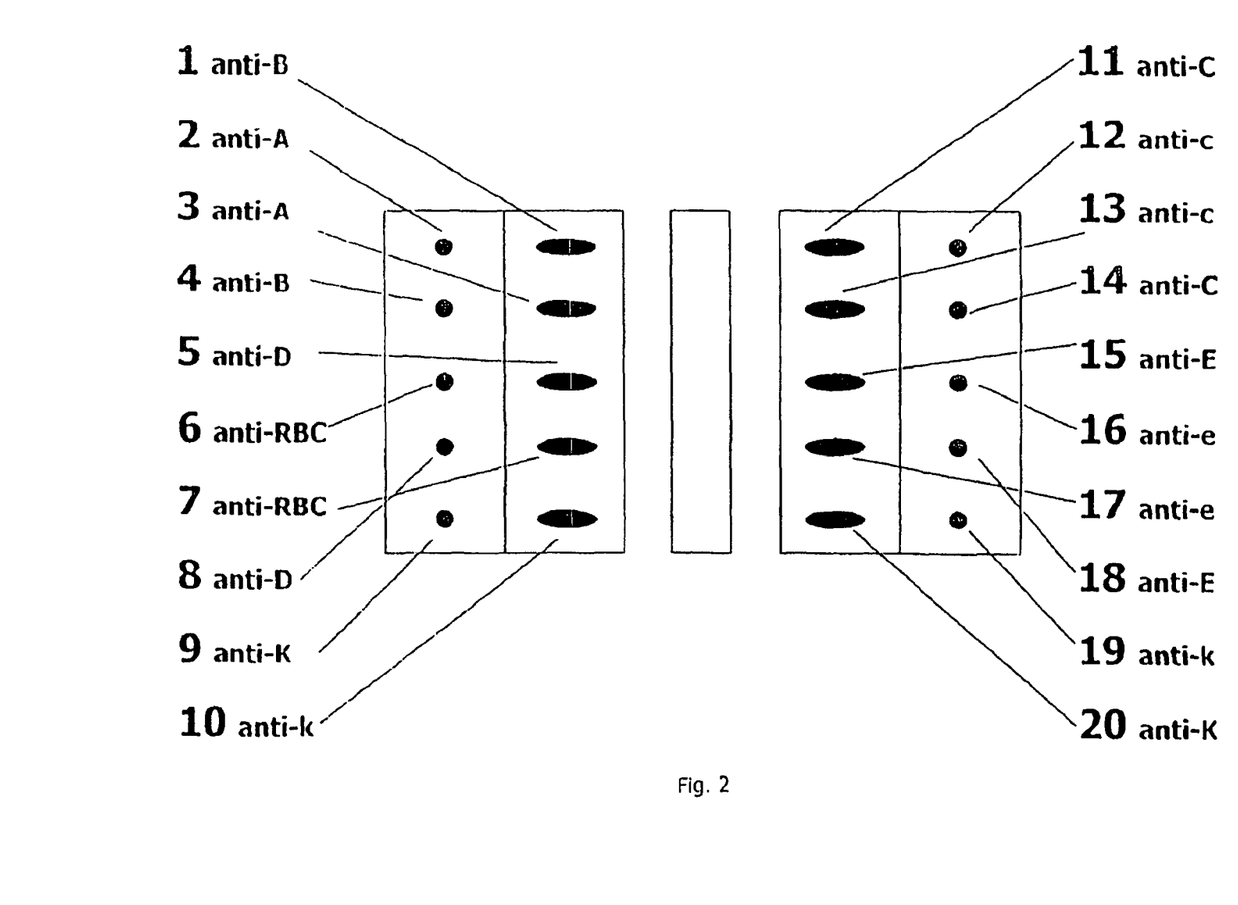
FIG. 2 depicts diagrammatically a possible application pattern for detecting mixed-field reactions.
Figure 3:
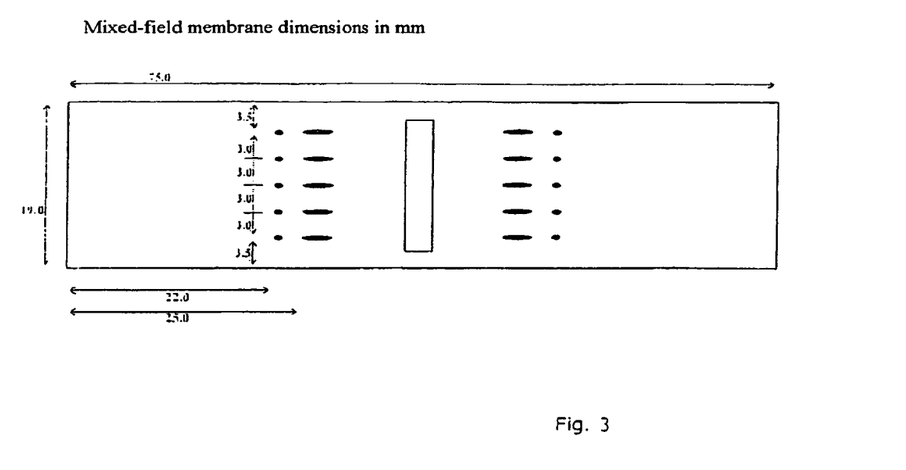
FIG. 3 depicts the possible dimensions of the application pattern described in FIG. 2 on a membrane suitable for detecting mixed-field reactions.

FIGS. 2 and 3 illustrate the design of a lateral flow device suitable for detecting a mixed-field reaction. Suitable dimensions can be found in FIG. 3, but these should be understood by way of example.

Whole Blood Test Mix:

50 µl of anticoagulated whole blood or freshly taken native blood are mixed with 200 µl of Diluent F (Medion Diagnostics). 100 µl of the resulting suspension are applied to the feeding zone. When the feeding zone has "run dry", 300 µl of Diluent F are applied.

Erythrocyte Sediment Test Mix:

50 µl of erythrocyte sediment (anticoagulated whole blood is centrifuged at 1500 rpm for 5 min; the erythrocyte sediment is located in the lower, red phase) are mixed with 400 µl of Diluent F. 100 µl of the resulting suspension are applied to the feeding zone. When the feeding zone has "run dry", 300 µl of Diluent F are applied.

The result can be read after approx. 5 minutes and is indicated by a slightly red wedge ("half moon"—minor cell population) up to a strongly red band or a strongly red spot (major cell population).

Figure 4:
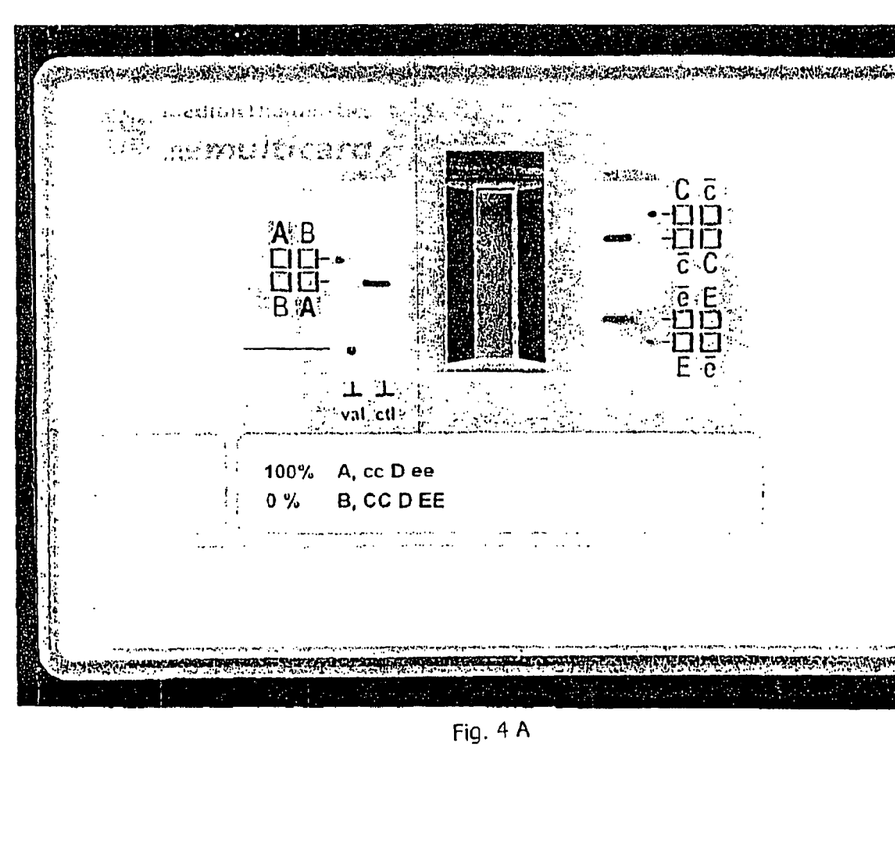
FIGS. 4A and 4B illustrate the detection of a mixed-field reaction with the aid of the two-indicator zone method according to the invention.

FIGS. 4A and 4B illustrate the detection of a mixed-field reaction with the aid of the two-indicator zone method of the invention. FIG. 4A here depicts the result of the examination of a blood sample with 100% A cc D. ee and 0% B CC D. EE. FIG. 4B depicts the result of the examination of a blood sample with 98% A cc D. ee and 2% B CC D. EE.

FIG. 4B depicts the detection of the minor cell population in the shape of a slight wedge (half moon) over the major cell population.

Example 2

Homologous Transfusion (Blood Doping)

The test strips were prepared in a manner similar to example 1.

| Proximal (line) | Distal (spot) |
|---|---|
| Anti-D → | Anti-RBC |
| Anti-RBC → | Anti-D |
| Anti-K → | Anti-k |
| Anti-k → | Anti-K |
| Anti-C → | Anti-c |
| Anti-c → | Anti-C |
| Anti-E → | Anti-e |
| Anti-e → | Anti-E |
| Anti-Jka → | Anti-Jkb |
| Anti-Jkb → | Anti-Jka |
| Anti-Cw → | Anti-RBC |
| Anti-RBC → | Anti-Cw |

Whole Blood Test Mix:

50 µl of anticoagulated whole blood or freshly taken native blood are mixed with 200 µl of Diluent F. 100 µl of the resulting suspension are applied to the feeding zone. When the feeding zone has "run dry", 300 µl of Diluent F are applied.

Erythrocyte Sediment Test Mix:

50 µl of erythrocyte sediment are mixed with 400 µl of Diluent F. 100 µl of the resulting suspension are applied to the feeding zone. When the feeding zone has "run dry", 300 µl of Diluent F are applied.

The result can be read after approx. 5 minutes and is indicated by a slightly red wedge ("half moon"—minor cell population) up to a strongly red band or a strongly red spot (major cell population).

Example 3

Detection of a Fetomaternal Hemorrhage (FMH)

The test strips were prepared as in example 1, with only anti-D being applied. Preference is given to applying individual antibodies rather than antibody mixtures. Preferred antibodies: RUM-1 (Millipore); LDM-3 (Alba Bioscience); or else ESD1M (Alba Bioscience); TH-28; MS-201; MS-26 (Millipore); LDM-1 (Alba Bioscience).

Test Mix a):

400 µl of anticoagulated whole blood or freshly taken native blood are mixed with 100 µl of Diluent F. 300 µl of the resulting suspension are applied to the feeding zone. When the feeding zone has "run dry", 400 µl of Diluent F are applied.

The result can be read after approx. 20 minutes and is indicated by a slightly red wedge (minor cell population) up to a strongly red band (major cell population).

Test Mix b): Similar to a), but Blood is Pretreated with Bromelase 3 ml of anticoagulated whole blood or freshly taken native blood are centrifuged at 1500 rpm for 3 min. Thereafter, 600 µl of the cell sediment are transferred to a second vessel and mixed therein with 600 µl of a commercial bromelain solution (e.g. Bromelase from Medion Diagnostics) and incubated at 37° C. for 15 min. This is followed by washing 3 times with 0.9% NaCl.

For the actual assay, 100 µl of the erythrocyte sediment bromelised and washed in this way are mixed with 200 µl of AB-Plasma and 200 µl of Diluent F (Medion Diagnostics). 300 µl of the resulting suspension are applied to the feeding zone. When the feeding zone has "run dry", 450 µl of Diluent F are applied.

The result can be read after approx. 15 minutes and is indicated by a slightly red wedge (minor cell population) up to a strongly red band (major cell population).

Example 4

Detection of an Erythrocytic Feature Present at an Extremely Low Antigen Density: DEL The test strips were prepared as in example 3. Preference is given to applying individual antibodies rather than mixtures. Preferred antibodies: RUM-1 (Millipore); LDM-3 (Alba Bioscience).

Test Mix a):

400 µl of anticoagulated whole blood or freshly taken native blood are mixed with 100 µl of Diluent F. 300 µl of the resulting suspension are applied to the feeding zone. When the feeding zone has "run dry", 400 µl of Diluent F are applied.

The result can be read after approx. 20 minutes and is indicated by a slightly red wedge (minor cell population) up to a strongly red band (major cell population).

Test Mix b): Similar to a), but Blood is Pretreated with Bromelase 3 ml of anticoagulated whole blood or freshly taken native blood are centrifuged at 1500 rpm for 3 min. Thereafter, 600 µl of the cell sediment are transferred to a second vessel and mixed therein with 600 µl of a commercial bromelain solution (e.g. Bromelase from Medion Diagnostics) and incubated at 37° C. for 15 min. This is followed by washing 3 times with 0.9% NaCl.

For the actual assay, 100 µl of the erythrocyte sediment bromelised and washed in this way are mixed with 200 µl of AB-Plasma and 200 µl of Diluent F (Medion Diagnostics). 300 µl of the resulting suspension are applied to the feeding zone. When the feeding zone has "run dry", 450 µl of Diluent F are applied.

The result can be read after approx. 15 minutes and is indicated by a slightly red wedge (minor cell population) up to a strongly red band (major cell population).

Example 5

Hematocrit

The test strips were prepared as in example 1, with serial application of in each case at least 2 (preferably 5) aliquots of the same antibody (anti-RBC). Variant 1: the antibody concentrations decrease from proximal to distal: variant 2: there are a plurality of flow tracks with in each case 2 (5) antibody spots, the antibody concentration decreasing from flow track to flow track; variant 3: combination of variant 1 and variant 2; variant 4: the proximal antibody application is a line, followed by a plurality of spots:

Application Example of Variant 2:

| Flow track 1 | anti-RBC anti-RBC anti-RBC anti-RBC anti-RBC (c = "1.0") |
|---|---|
| Flow track 1: | anti-RBC anti-RBC anti-RBC anti-RBC anti-RBC (c = "0.8") |
| Flow track 1: | anti-RBC anti-RBC anti-RBC anti-RBC anti-RBC (c = "0.6") |
| Flow track 1: | anti-RBC anti-RBC anti-RBC anti-RBC anti-RBC (c = "0.4") |
| Flow track 1: | anti-RBC anti-RBC anti-RBC anti-RBC anti-RBC (c = "0.2") |

Whole Blood Test Mix:

50 µl of anticoagulated whole blood or freshly taken native blood are mixed with 200 µl of Diluent F. 100 µl of the resulting suspension are applied to the feeding zone. When the feeding zone has "run dry", 300 µl of Diluent F are applied.

Figure 5:
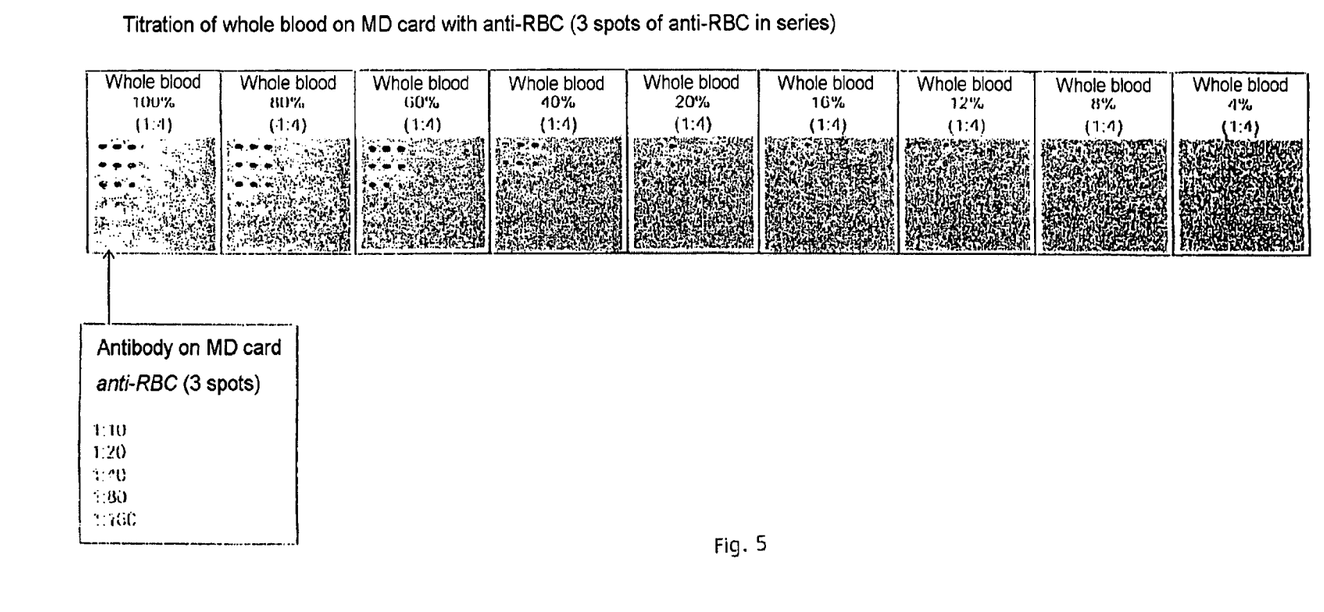
FIG. 5 depicts the determination of the hematocrit value with the aid of the method according to the invention.

The result can be read after approx. 5 minutes (cf. FIG. 5).

Erythrocyte Sediment Test Mix:

50 µl of erythrocyte sediment are mixed with 400 µl of Diluent F. 100 µl of the resulting suspension are applied to the feeding zone. When the feeding zone has "run dry", 300 µl of Diluent F are applied.

The result can be read after approx. 5 minutes (cf. FIG. 5).

The invention claimed is:

1. A method for quantifying a minor erythrocyte cell population in heterogeneous erythrocyte cell populations or for detecting an analyte which is present at a low concentration on erythrocyte cells, comprising the steps of:
a) mixing an amount of a blood sample with a diluent to provide a liquid sample, wherein the concentration of the minor erythrocyte cell population, based on the total heterogeneous erythrocyte cell population, is less than 1% or wherein the analyte is present in less than 30 antigens per erythrocyte cell and wherein the amount of the diluent is lower than or equal to the amount of the blood sample;
b) applying approximately from 200 µl to 500 µl of the liquid sample containing cells of step a) to a feeding zone;
c) applying the diluent;
d) performing an assay comprising incubating the liquid sample of step a) with the test device such that the applied sample migrates from the feeding zone through indicator zones to an absorption region;
e) concentrating the minor erythrocyte cell population by binding to the indicator zone and decreasing the amount of further erythrocyte cell populations at this indicator zone; and
f) evaluating the assay by determining whether erythrocyte cells are bound to the indicator zone;
said method being carried out using a device comprising:
at least one feeding zone (5) for applying the liquid sample containing cells,
a porous membrane (2) that is suitable for being penetrated by cellular components and that includes at least one indicator zone on the membrane, which indicator zone interacts with cellularly bound analyte in the liquid sample and contains at least one binding element against the cellularly bound analyte, and
at least one absorption region (3) on the membrane, which absorbs the liquid sample after the latter has passed the indicator zone,
wherein the at least one indicator zone is located between the feeding zone (5) and the absorption region (3).

2. The method as claimed in claim 1, which is carried out for determining fetomaternal hemorrhage (FMH), wherein the sample contains erythrocytes, wherein the indicator zone contains an antibody or an antibody mixture.

3. The method as claimed in claim 1, which is carried out for determining an analyte which is present at a low concentration on cells, wherein the analyte is DEL, and wherein the indicator zone contains an antibody or an antibody mixture.

4. The method of claim 1, which further comprises, prior to step a), preparing an erythrocyte sediment by centrifuging a blood sample; incubating the sediment with a bromelain, papain or ficin solution; and resuspending the enzyme-treated sediment.

5. The method of claim 1, wherein approximately from 100 µl to 200 µl of the diluent is applied in step c).

6. The method of claim 1, wherein the indicator zone contains an anti-D antibody, and the anti-D antibody is selected from RUM-1, LDM-3, ESD1M, TH-28, MS-201, MS-26 and LDM-1.

7. The method of claim 1, wherein the device contains at least two indicator zones which are arranged one behind the other in the direction of flow in such a way that the sample liquid passes through more than one indicator zone in each flow track, wherein the indicator zones contain binding elements against cellularly bound analytes, wherein the sample is a blood sample containing erythrocytes, and the assay is evaluated by determining whether erythrocytes are bound to the indicator zone(s), and wherein the method is carried out for determining in parallel cellularly bound analytes in cases of fetomaternal hemorrhage (FMH), for determination in mixed-field reactions, or for detecting a homologous transfusion or for determining the hematocrit value.

8. The method of claim 7, which is carried out for detecting a homologous transfusion.

9. The method of claim 8, wherein the device contains at least two indicator zones arranged in a single flow track, and wherein the indicator zones contain identical binding elements against the same cellularly bound analyte.

10. The method of claim 8, wherein the device has at least two flow tracks containing at least two indicator zones, and the concentration of the binding element increases or decreases from proximal to distal, in relation to the feeding zone.

11. The method of claim 8, wherein the device has at least two flow tracks containing at least two indicator zones, and the concentration of the antibody in a first flow track differs from the concentration in a second flow track.

12. The method of claim 7, which is carried out for determining in parallel cellularly bound analytes in mixed-field reactions or for detecting a homologous transfusion, wherein the device contains at least two indicator zones which are arranged one behind the other in the direction of flow in such a way that the sample liquid passes through more than one indicator zone in each flow track, wherein the indicator zones contain binding elements against different cellularly bound analytes.

13. The method of claim 1, wherein the cellularly bound analyte is selected from a blood group antigen A, B, AB, D, C, c, E, e, Cw, K, k, Jka and/or Jkb.

14. The method as claimed in claim 13, wherein the blood group antigens are determined by way of the reaction pairs A, B; D+, D−; K, k; C, c and/or E, e.

15. The method as claimed in claim 1, wherein the binding element directed against the analyte is selected from an antibody, antibody fragment, lectin, lectin fragment or mixtures thereof.

16. The method as claimed in claim 1, wherein the membrane or the membranes (2) consist of polyethylene, nitrocellulose or nylon.

17. The method as claimed in claim 1, wherein at least one sealing element (4) is arranged downstream of the feeding zone (5) and upstream of the indicator zones on the membrane (2).

18. The method as claimed in claim 1, wherein the feeding zone (5), porous membrane (2), and absorption region (3) of the device are applied to a support layer (1) for mechanical reinforcement.

19. The method as claimed in claim 1, wherein the feeding zone (5), porous membrane (2), and absorption region (3) of the device are integrated in a housing.

20. The method as claimed in claim 2, wherein approximately from 200 µl to 500 µl of a blood sample or resuspended erythrocyte sediment is applied in step a).

21. The method as claimed in claim 1, wherein the concentration of the minor erythrocyte cell population, based on the total heterogeneous erythrocyte cell population, is 0.1% or less.

* * * * *